United States Patent [19]

Shinohara et al.

[11] 4,455,280
[45] Jun. 19, 1984

[54] APPARATUS FOR PRESERVING LIQUID IN AUTOMATIC ANALYZER

[75] Inventors: Toshio Shinohara, Chofu; Masao Usikubo, Hachioji, both of Japan

[73] Assignee: Olympus Optical Co. Ltd., Japan

[21] Appl. No.: 345,155

[22] Filed: Feb. 2, 1982

[30] Foreign Application Priority Data

Feb. 10, 1981 [JP] Japan .................................. 56-16656

[51] Int. Cl.³ .......................................... G01N 35/00
[52] U.S. Cl. ...................................... 422/63; 141/65; 141/154; 141/350; 422/64; 422/65; 422/100; 422/102; 422/104
[58] Field of Search .................................. 422/63-67, 422/99, 100, 102, 104; 141/65, 82, 154, 350

[56] References Cited

U.S. PATENT DOCUMENTS

| | | | |
|---|---|---|---|
| 3,098,721 | 7/1963 | Jewell | 422/99 |
| 3,191,640 | 6/1965 | Hackett | 422/102 |
| 3,993,452 | 11/1976 | Moulding | 422/104 |
| 4,276,258 | 6/1981 | Ginsberg et al. | 422/64 |
| 4,338,279 | 7/1982 | Orimo et al. | 422/64 |

FOREIGN PATENT DOCUMENTS 7208758  1/1973  Netherlands ....................... 422/104

Primary Examiner—Michael S. Marcus
Attorney, Agent, or Firm—Parkhurst & Oliff

[57] ABSTRACT

In an apparatus for preserving different kinds of reagents to be selectively delivered for performing different test items in an automatic chemical analyzer, the reagents are contained in respective vessels which are placed on a turntable rotatably arranged in a compartment inside of which is kept at a low temperature, beside each reagent container is movably arranged a plug plate having an elastic plug secured thereto and a movable lever is arranged to engage with any one of the plug plate so as to remove the plug out of an opening of the reagent vessel only when a probe of a delivery device is moved through the opening.

6 Claims, 3 Drawing Figures

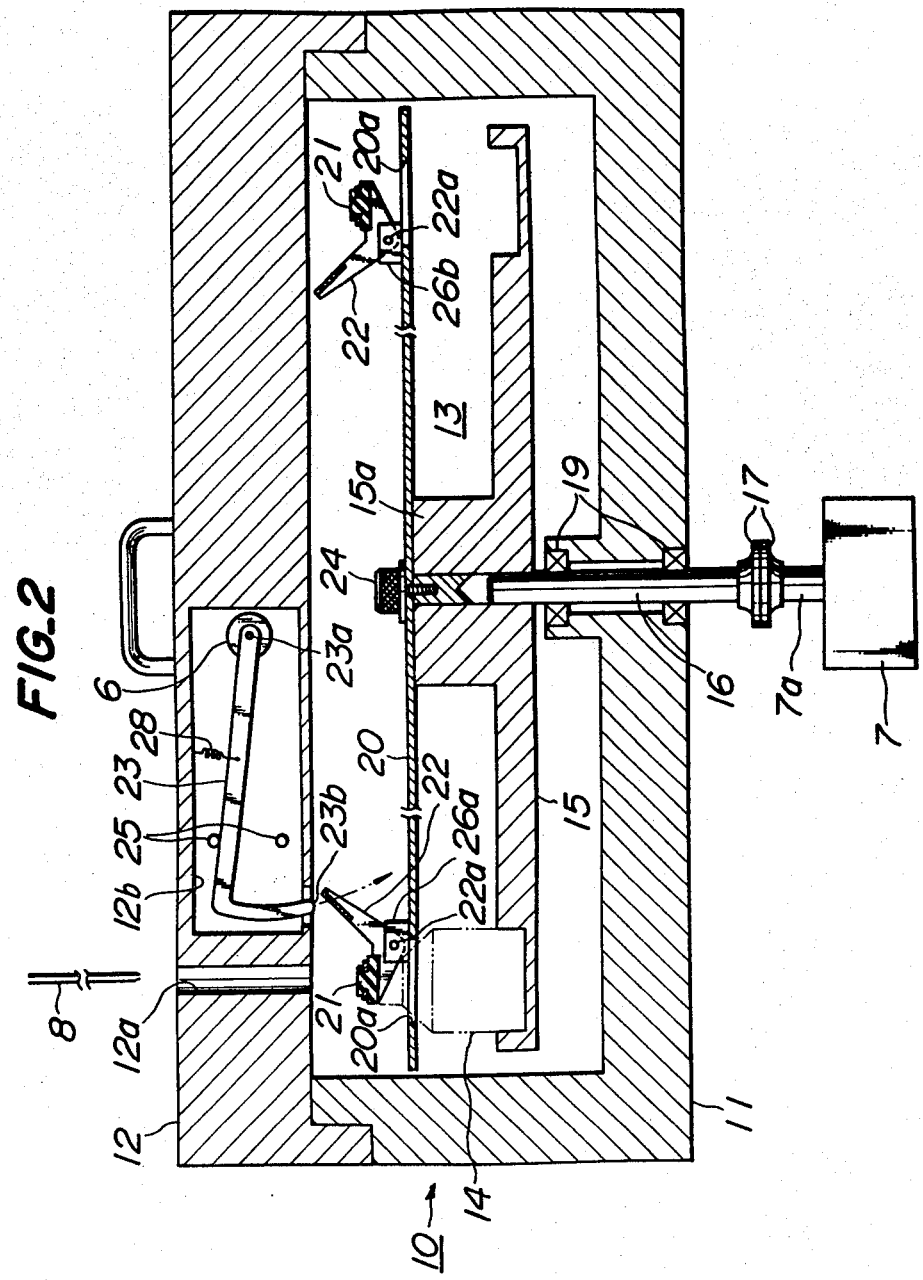

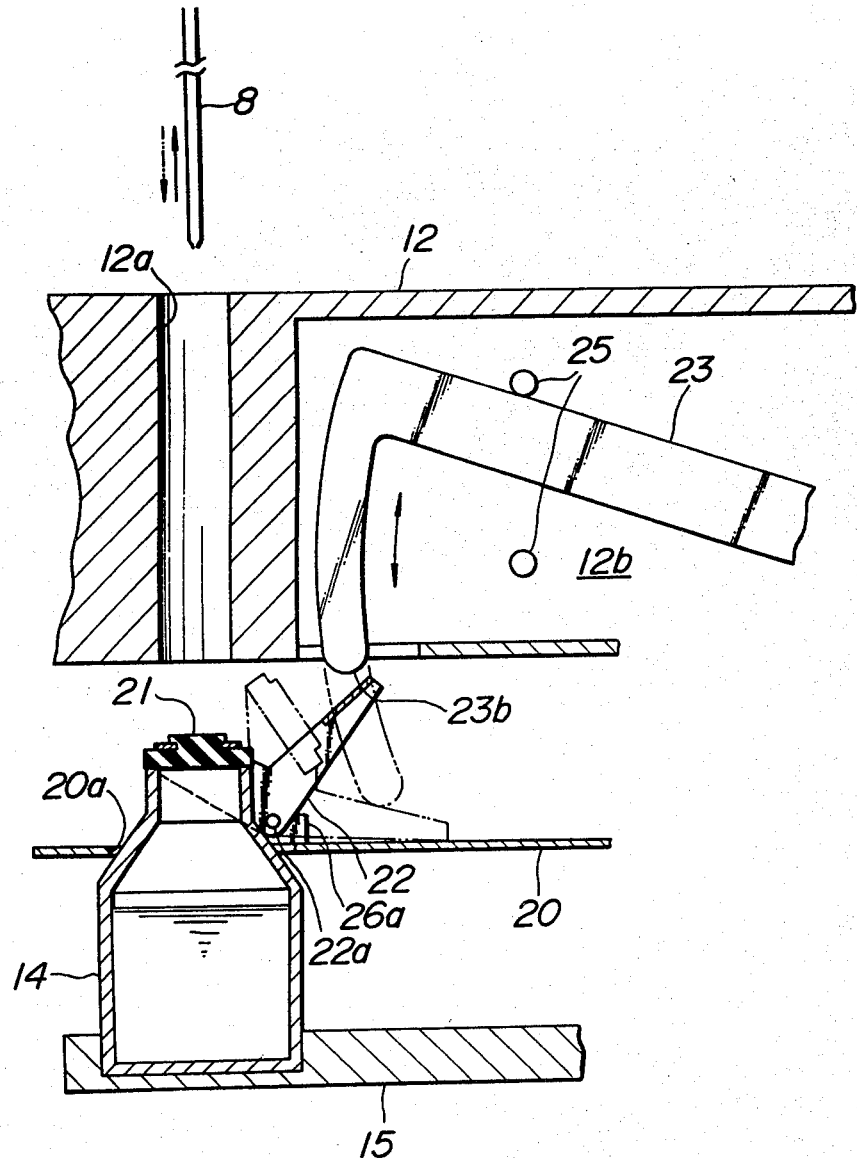

APPARATUS FOR PRESERVING LIQUID IN AUTOMATIC ANALYZER

BACKGROUND OF THE INVENTION

This invention relates to an apparatus for preserving at least one kind of liquid such as sample, reagent, buffer solution, and diluent to be delivered in an automatic chemical analyzer.

In a usual automatic chemical analyzer, in order to effect multi-item test, a plurality of reagents are preserved. Usually each reagents are contained in respective containers. There are two types of a reagent delivery mechanisms. In one type of mechanism, usually only one delivery device is provided and a given amount of a given reagent is aspirated into a probe and the aspirated reagent is discharged from the probe into a reaction vessel. In the other type, there are arranged a plurality of delivery devices, one end of each probe is connected to respective reagent container via a respective pump and a given amount of a given reagent is supplied through an entire length of the probe into a reaction vessel. In the former delivery mechanism, the reagent container has to be provided with an opening through which the probe passes, and thus, the reagent is liable to evaporate into a surrounding atmosphere through said opening. Contrary to this, in the later delivery mechanism, since such an opening is not required, the problem of evaporation does not occur. However, in the later mechanism, a number of delivery devices equal to the number of the reagent containers must be provided and the apparatus is liable to be complicated in construction and large in size. The present invention concerns the liquid preserving apparatus for use in a combination of the former type delivery mechanism.

In case of preserving the reagents in the analyzer, it is necessary to preserve the reagents in a cooling state in a temperature range of about 5°–10° C. for preventing the quality of reagent from being deteriorated. To this end, usually the reagent containers are arranged in a compartment and temperature in the compartment is lowered. However, since the air surrounding the reagent containers becomes low humidity in such a cooling state, the reagents are liable to evaporate and thus their concentrations might be changed. Moreover, in case that a plurality kinds of the reagents are arranged in the same compartment, there might occur such a drawback that acid components evaporated from the reagents might affect the quality of another reagents. Further the inside of the compartment might rust due to various components evaporated from the reagents.

In order to avoid the above mentioned evaporation, it has been proposed to seal the openings of the reagent containers with covers made of elastic material such as plastics and rubber, and the probe pierces the cover to suck the reagent. In such a case after the probe is removed from the cover, a hole in the cover is automatically closed due to its elasticity. However, in such a construction it is necessary to make the probe and a mechanism for supporting the probe mechanically strong. For instance, the probe must be made of metal and the probe holding device is liable to be large and heavy. Moreover, there is such a possibility that the probe might be clogged by chips of the cover, and this results in that a delivering precision becomes worse.

In U.S. Pat. No. 4,208,484, there is described an automatic culture system in which a space surrounding a centrifuge is shielded from the outer atmosphere and an opening through which centrifuge tube is passed is selectively closed by a movable cover. This system may be applied to the compartment of the reagent containers. That is to say, an opening formed in the compartment for introducing the probe may be closed by a movable cover. However, even in such a construction, the reagents might evaporate within the space and thus, the above mentioned problem could be overcome only to a limited extent.

SUMMARY OF THE INVENTION

The present invention has for its object to provide a novel and useful apparatus for preserving liquids to be delivered in the automatic chemical analyzer, which apparatus can avoid the aforesaid drawbacks and can preserve the liquids without deterioration thereof.

It is still another object of the invention to provide a liquid preserving apparatus which can prevent a compartment for keeping reagent containers at a low temperature from being rusted by components evaporated from reagents.

According to the invention, an apparatus for preserving at least one kind of liquid to be delivered by a delivery device including a probe for aspirating and discharging a given amount of the liquid in an automatic chemical analyzer, comprises means for containing said liquid and having an opening through which said probe is movable into and out of the liquid;

means for closing said opening of the liquid containing means; and means for removing said closing means out of said opening during a delivering operation so as to allow the passage of the probe through said opening.

BRIEF DESCRIPTION OF THE DRAWINGS

FIG. 2 is a longitudinal sectional view illustrating one embodiment of the reagent preserving apparatus according to the invention; and FIG. 3 is an enlarged longitudinal sectional view of a part of the apparatus illustrated in FIG. 2.

DESCRIPTION OF THE PREFERRED EMBODIMENTS

Figure 1:
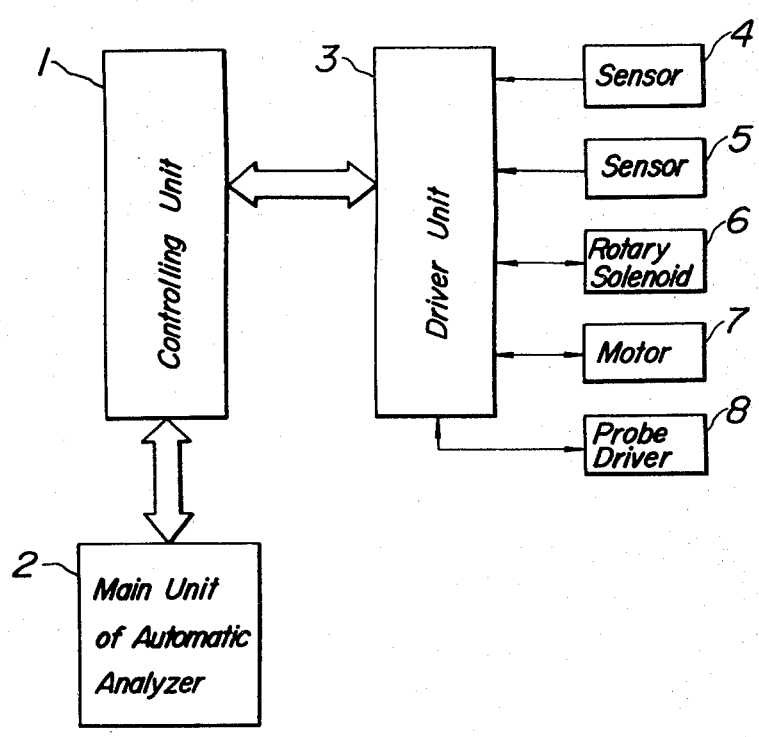
FIG. 1 is a block diagram showing a whole construction of an automatic chemical analyzer including a reagent preserving apparatus according to the invention.

FIG. 1 is a block diagram showing a construction of an automatic chemical analyzer comprising the reagent preserving apparatus according to the invention. A controlling unit 1 is connected to a main unit 2 of the automatic chemical analyzer and a driver unit 3 including D/A and A/D converters, interfaces, etc. To the driver unit 3 are connected a sensor 4 for detecting positions of a plurality of reagent vessels placed on a turntable, a sensor 5 for detecting kinds of reagents, a rotary solenoid 6 for moving a cover to open and close an opening of the reagent vessel, a motor 7 for rotating the turntable for holding the reagent vessels to index a reagent vessel containing a given reagent to be delivered into an aspirating position of a delivery device and a probe driver 8 for moving a probe of the delivery device.

FIGS. 2 and 3 are longitudinal sectional views illustrating one embodiment of the reagent preserving apparatus according to the invention. The apparatus comprises a compartment 10 containing a plurality of reagent vessels 14. The compartment comprises a housing 11 formed by a heat insulator and an upper lid 12 which is fitted to the housing 11. An inner space 13 formed by the housing 11 and lid 12 constitutes a cooling room. In this cooling room 13 is arranged a turntable 15 on which a plurality of the reagent vessels 14 may be placed. The turntable 15 is coupled with a shaft 16 and the shaft 16 is connected to a rotating shaft 7a of the motor 7 by means of a pair of flanges 17, so that the turntable 15 is rotated by the motor 7 through the rotating shaft 7a, the flange 17, and the shaft 16. Moreover, a projection 15a is formed at a center of the turntable 15. The shaft is rotatably mounted by a pair of ball bearings 19 arranged at a center of the housing 11. Furthermore, an intermediate lid 20 is detachably secured to the center projection 15a by means of knurled screw 24 so as to divide the cooling room 13 into two sections. The cold air is supplied into the lower section from a suitable cooling source not shown. As shown in FIG. 2, a substantial portion of the reagent vessel 14 is situated in the lower section of cooling room 13. Therefore, almost all portion of the vessel 14 is exposed to a cold air, and the cold air does hardly escape from the lower section into the upper section, the cooling can be effected efficiently and the evaporation of the reagents can be minimized. The intermediate lid 20 has a plurality of holes 20a formed therein. Beside each hole 20a, is arranged a movable cover assembly comprising a plug 20 secured to a plug plate 22 which is rotatably supported by a pair of projecting members 26a, 26b and a shaft 22a. In order to close the opening of the reagent vessel 14 airtightly by the plug 21, the plug is preferably made of elastic material such as rubber and plastics. Between the plug plate 22 and the projection 26a is arranged a coiled spring to rotate the plug plate 22 in anti-clockwise direction. This rotation is limited by a suitable stopper not shown. In the upper lid 12 there is formed a hollow space 12b in which a lever 23 is arranged movably about a shaft 23a which is connected to a rotary solenoid 6. By emergizing the rotary solenoid, the lever 23 is swung about the shaft 23a within a desired angle range defined by a pair of stoppers 25. Then, the plug plate 22 is rotated against the spring force by the engagement with a tip portion 23b of the lever 23 so as to remove the plug 21 out of the opening of the reagent vessel 14. Then, the probe 8 is moved downward into the cooling room 13 through a hole 12a formed in the upper lid 12 to suck a given amount of the reagent in the reagent vessel 14 situating at the aspirating position. After sucking the predetermined amount of the reagent and moving the probe upward out of the cooling room 13, the rotary solenoid 6 is de-energized under control of the control unit 1 so that the lever 23 is returned to the original position by an elastic force of a spring 28. When the lever 23 is rotated in the clockwise direction, the plug plate 22 is rotated in the anti-clockwise direction so that the opening of the reagent vessel 14 is closed again airtightly by the plug 21. During this process, the remaining plugs are left stationary and thus, unnecessary evaporation can be avoided.

The delivery operation of the above mentioned apparatus will be explained hereinafter also with reference to FIG. 1. In case of delivering a given reagent to be used for effecting a desired test item, the reagent vessel 14 containing said given reagent is indexed at the aspirating position while detecting the kinds and positions of the reagent vessels by means of the sensors 4, 5, and the detected signals are supplied to the controlling unit 1 through the driver unit 3. Then, the motor 7 is actuated on the basis of the detected signals so as to rotate the turntable 15. Finally, the turntable 15 is stopped at a predetermined position under the control of the controlling unit 1. When the given reagent vessel 14 has been indexed to the predetermined aspirating position, a synchronizing signal is supplied to the controlling unit 1 to actuate the rotary solenoid 6, and then the lever 23 is rotated in the anti-clockwise direction as shown by an arrow. As shown in FIG. 3, during this movement the tip portion 23b of the lever 23 is engaged with the plug plate 22 and the plate is driven into a position shown by a double-dotted chain line in FIG. 3. Then the probe 8 is moved downward as shown by a double-dotted chain line through the hole 12a under the control of the controlling unit 1 and then is immersed into the given reagent in the vessel 14. Then a predetermined amount of the given reagent is aspirated into the probe 8. Further, the probe 8 is moved upward through the hole 12a and the aspirated reagent is discharged into a reaction vessel not shown. After the probe 8 has been removed out of the compartment 10, the lever 23 is returned to the original position by means of the spring 28, and then the opening of the reagent vessel 14 is sealed again airtightly, because the plug plate 22 is also returned to the original position by means of the spring not shown. In this manner, the openings of the reagent vessels are closed almost all time and thus, the evaporation of the reagents can be effectively avoided.

The present invention is not limited to the embodiment mentioned above, but various modifications and alternations are possible. For example, in the embodiment mentioned above, the sample vessels are moved with respect to the aspirating position, but the reagent vessels may be arranged stationary and the probe may be moved. In this cse, in the upper lid 12 there must be formed a plurality of holes through which the probe is passed at positions corresponding to each vessels. These holes may be replaced by a smaller number of a large hole or holes. Moreover, as for the rotating mechanism for turntable supporting the reagent vessels, use is preferably made of a pulse motor. Further, it is also possible to use a linearly moving mechanism such as conveyor belt. Furthermore, in the embodiment mentioned above, each openings of the reagent vessels are closed by the respective plugs, but it is possible to close the openings of a plurality of reagent vessesls by a large lid at the same time. Moreover, the liquid is not limited to the reagents but may be any other solutions such as sample liquid, diluent, buffer solutions whose physical or chemical property might be changed by evaporation or whose evaporated components might affect another solution. Furthermore, in the embodiment mentioned above, the compartment is cooled, but according to kind of liquid to be used it is possible to keep the inside of the compartment at the room temperature or at a higher temperature. In case of keeping the liquid at the room temperature, it is not necessary to arrange the compartment.

As mentioned above according to the invention, the following advantageous effects can be achieved. (A) It is possible to prevent a variation in concentration of the reagents due to evaporation. (B) It is possible to prevent a corrosion of the compartment due to evaporation of harmful components of the reagents. (C) It is possible to prevent mutual influence between the reagents due to evaporation thereof.

What is claimed is:

1. An apparatus for preserving and delivering liquids to be delivered by a delivery device including a probe for aspirating and discharging a given amount of liquid in an automatic chemical analyzer, each liquid being contained in respective liquid containers, comprising:
   a compartment including a housing and an upper lid which is detachably fitted to the housing;
   a turntable arranged rotatably in said housing and having a plurality of positions for locating a plurality of said liquid containers;
   means for keeping a temperature inside the compartment at a desired temperature;
   means for rotating the turntable for indexing a desired one of said plurality of liquid containers at a liquid aspirating position;
   a hole formed in the upper lid at said liquid aspirating position, said probe of the delivery device being insertable through said hole;
   a plurality of movable plug assemblies provided on the turntable, each of the plug assemblies being movable between a closed position for closing an opening of a respective liquid container and an open position for exposing the opening of a respective liquid container; and
   removing means comprising a member movably secured to the upper lid and having an actuating end which is selectively engaged with a movable plug assembly for moving the movable plug assembly from the closed position to the open position, thereby exposing the opening of a liquid container indexed at the aspirating position.

2. An apparatus according to claim 1, wherein each said liquid containers contain a reagent.

3. An apparatus according to claim 1, further comprising an intermediate lid detachably secured to said turntable and having a plurality of openings through which upper parts of said liquid containers extend, the inside space of the compartment being divided into upper and lower sections by said intermediate lid and substantial portions of the liquid containers being situated in the lower section which is kept at a desired temperature.

4. An apparatus according to claim 3, wherein said plurality of movable plug assemblies are arranged at respective openings of the intermediate lid.

5. An apparatus according to claim 4, wherein each of said movable plug assemblies comprises a plug made of elastic material for closing the opening of the liquid container, a plug plate journaled swingably to the intermediate lid and having one end secured to the plug, and said member of the removing means comprises an L-shaped lever having one end which is engaged with the other end of said plug plate and the other end connected to a rotary member.

6. An apparatus according to claim 5, wherein said rotary member comprises a rotary solenoid.

* * * * *